US00PP36848P2

(12) United States Plant Patent
Martens et al.

(10) Patent No.: US PP36,848 P2
(45) Date of Patent: Jul. 22, 2025

(54) ***PRUNUS* PLANT NAMED 'Frerichs 01'**

(50) Latin Name: *Prunus laurocerasus*
Varietal Denomination: Frerichs 01

(71) Applicants: Ocko Martens, Westerstede/Hoheliet (DE); Pascal Frerichs, Westerstede/Hoheliet (DE)

(72) Inventors: Ocko Martens, Westerstede/Hoheliet (DE); Pascal Frerichs, Westerstede/Hoheliet (DE)

( * ) Notice: Subject to any disclaimer, the term of this patent is extended or adjusted under 35 U.S.C. 154(b) by 0 days.

(21) Appl. No.: 19/048,852

(22) Filed: Feb. 8, 2025

(51) Int. Cl.
*A01H 6/74* (2018.01)
*A01H 5/02* (2018.01)

(52) U.S. Cl.
USPC ..... Plt./226

(58) Field of Classification Search
USPC ..... Plt./226
CPC ..... A01H 6/7427; A01H 5/02
See application file for complete search history.

*Primary Examiner* — Keith O. Robinson
(74) *Attorney, Agent, or Firm* — Penny J. Aguirre

(57) ABSTRACT

A new cultivar of *Prunus laurocerasus* plant named 'Frerichs 01' that is characterized by its vigorous growth habit, its narrowly upright plant habit, its dense branching, and its young foliage that is intense bronze to orange in color.

3 Drawing Sheets

Botanical classification: *Prunus laurocerasus.*
Variety denomination: 'Frerichs 01'.

CROSS REFERENCE TO A RELATED APPLICATION

This application is related to a European plant breeders' rights application filed on Dec. 24, 2021, application No. 2021/3454. The information for the Plant Breeders' Right Application was directly received from the Inventors.

BACKGROUND OF THE INVENTION

The present invention relates to a new and distinct cultivar of *Prunus laurocerasus* and will be referred to hereafter by its cultivar name, 'Frerichs 01'. 'Frerichs 01' is a new cultivar of English laurel grown for use as a landscape plant and particularly useful as a hedge plant.

The new cultivar was discovered by one of the Inventors in June of 2018 as a naturally occurring branch mutation of *Prunus laurocerasus* 'Novita' (not patented) growing outdoors in a nursery production field in Westerstede/Hoheliet, Germany.

Asexual propagation of the new cultivar was first accomplished by stem cuttings by the Inventors in Westerstede/Hoheliet, Germany in June 2018. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Frerichs 01' as a unique cultivar of English laurel.

1. 'Frerichs 01' exhibits a vigorous growth habit.
2. 'Frerichs 01' exhibits a narrowly upright plant habit.
3. 'Frerichs 01' exhibits dense branching.

4. 'Frerichs 01' exhibits young foliage that is intense bronze to orange in color.

The female parent of 'Frerichs 01' differs from 'Frerichs 01' in having young foliage that is green in color and in being less densely branched. 'Frerichs 01' can be most closely compared to the *Prunus* cultivars 'Anbri' (not patented) and 'Chamaeleon' (not patented). 'Anbri' is similar to 'Frerichs 01' in having young foliage shoots that are bronze to orange in color. 'Anbri' differs from 'Frerichs 01' in having a broader plant shape, a less vigorous growth habit, and leaves that are shorter and broader. 'Chamaeleon' is similar to 'Frerichs 01' in having an upright growth habit. 'Chamaeleon' differs from 'Frerichs 01' in having a broader plant habit, a less vigorous growth habit, leaf apices that are more round in shape, young foliage shoots that are less intensely bronze-orange in color, and less winter hardiness.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by Van Vliet New Plants an Plantago.

BRIEF DESCRIPTION OF THE DRAWINGS

The accompanying color photographs illustrate the overall appearance and distinct characteristics of the new *Prunus*. The photographs were taken of a 36-month-old tree as grown outdoors in a 28-cm container in Achtmaal, The Netherlands.

The photograph in FIG. 1 provides a side view of the overall plant habit of 'Frerichs 01'.

Figure 1:
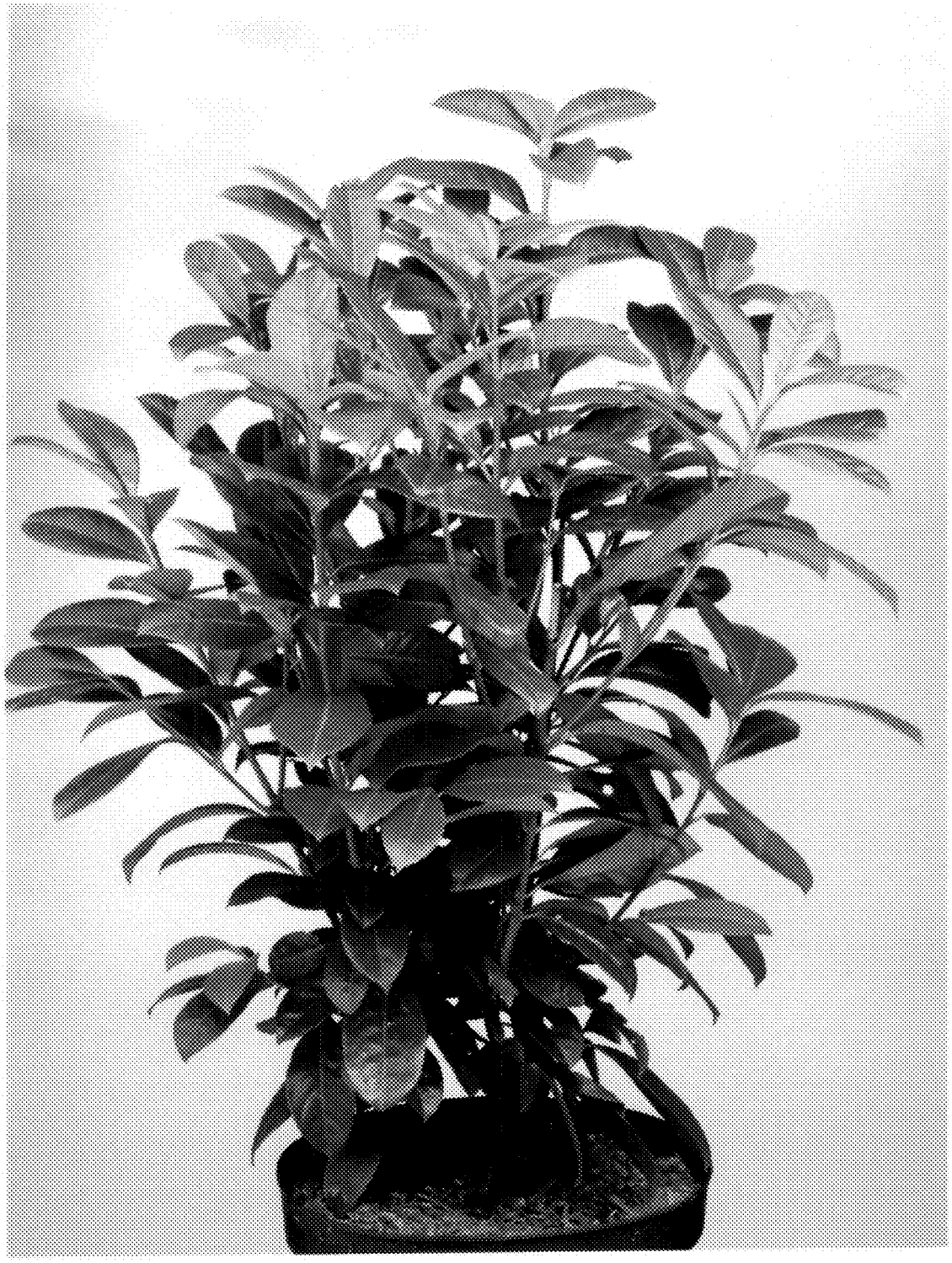
Figure 2:
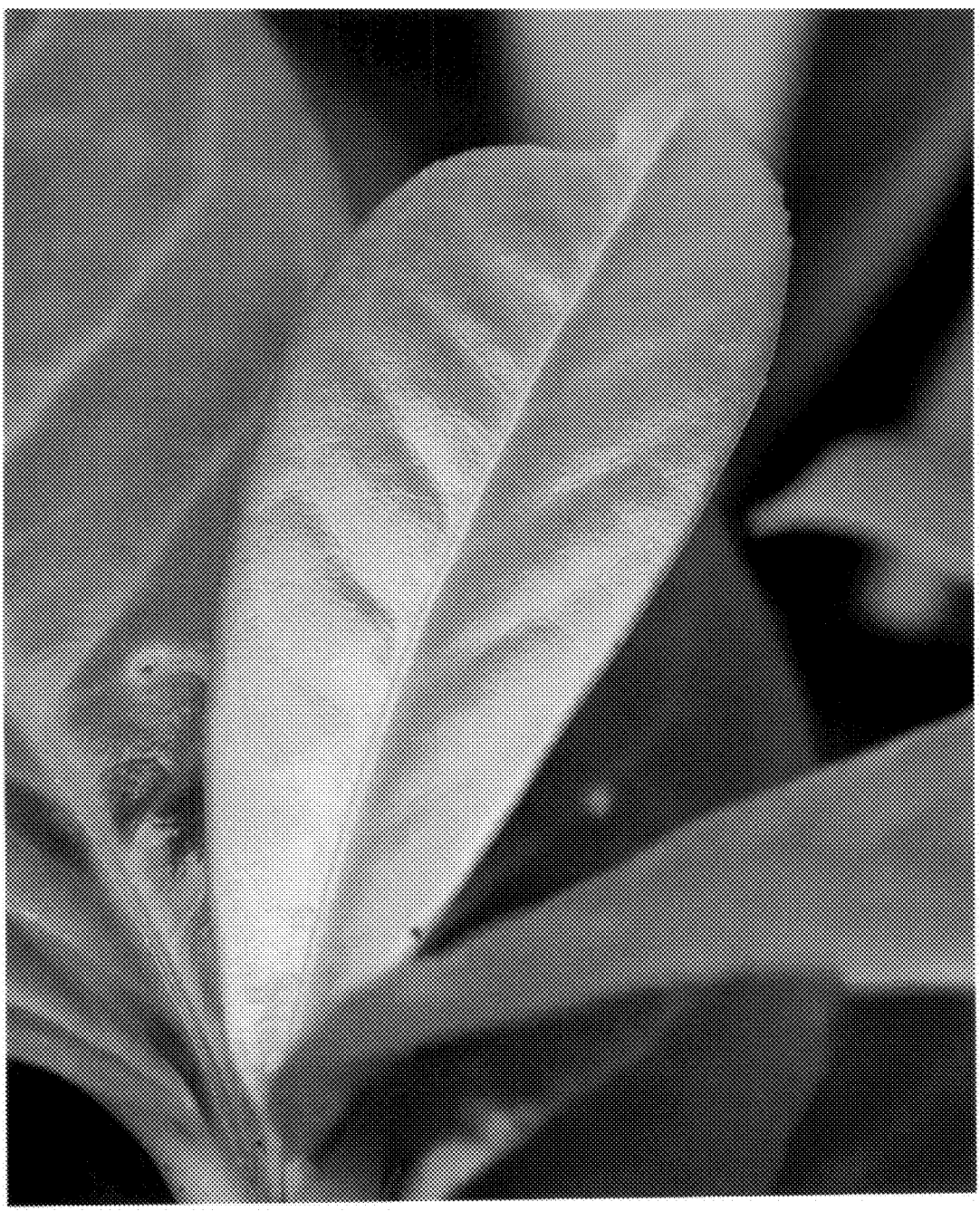

The photograph in FIG. 2 provides a close-up view of the young foliage of 'Frerichs 01'.

Figure 3:
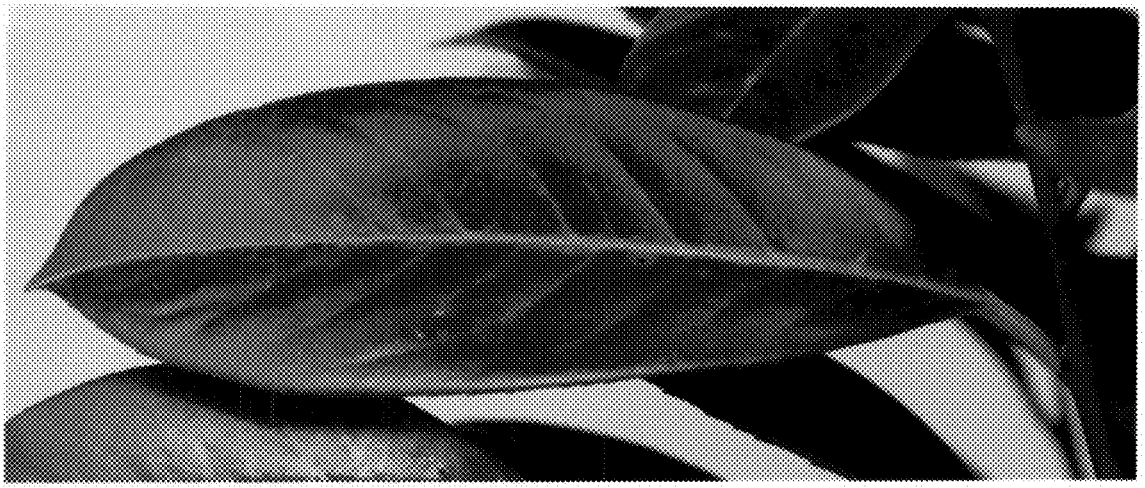

The photograph in FIG. 3 provides a close-up view of the mature foliage of 'Frerichs 01'.

The colors in the photographs are as close as possible with the photographic and printing technology utilized and the color values cited in the Detailed Botanical Description accurately describe the colors of the new *Prunus*.

DETAILED BOTANICAL DESCRIPTION

The following is a detailed description of 36-month-old trees as grown outdoors in a 28-cm container in Achtmaal, The Netherlands. The phenotype of the new cultivar may vary with variations in environmental, climatic, and cultural conditions, as it has not been tested under all possible environmental conditions. The color determination is in accordance with the 2015 $6^{th}$ edition (2019 reprint) Colour Chart of The Royal Horticultural Society, London, England, except where general color terms of ordinary dictionary significance are used.

General description:

*Plant type*.—Herbaceous deciduous evergreen shrub.

*Plant habit*.—Narrowly upright.

*Height and spread*.—Average of 73 cm in height, 56 cm in spread as a 36-month-old plant grown in a container, reaches an average of 3 m in height and 1.5 m in spread in the landscape.

*Hardiness*.—At least in U.S.D.A. Zones 6 to 10.

*Diseases and pests*.—No susceptibility or resistance to diseases or pests has been observed.

*Root description*.—Fibrous, freely branched.

*Root development*.—3 to 4 months to initiate roots, 5 to 6 months to produce a rooted cutting.

*Propagation*.—Stem cuttings.

*Growth rate*.—Vigorous.

Branch description:

*Branch size*.—44.6 cm in length, 6.5 mm in diameter.

*Branch shape*.—Rounded, young stems slightly to moderately 5-sided at the top.

*Branch color*.—Young; 144A to 144B, densely covered with small lenticels N167B, mature; a blend of NN137A, 197B, and 197C, older branches and bark; 200A, axially striped 166C.

*Branch surface*.—Matte to very slightly glossy, densely covered with small lenticels 0.2 mm in diameter.

*Branch aspect*.—Held in an average angle of 45°.

*Branching habit*.—Densely branched, average of 3 main branches and 7 lateral branches per main branch.

*Branch internode length*.—Average of 3.4 cm.

Foliage description:

*Leaf shape*.—Obovate to obovate-oblong.

*Leaf division*.—Simple.

*Leaf base*.—Acute, glands are near the base on the lower surface, an average of 2 to 4, occasionally 5 close to the main vein, average of 1.5 mm, 200A and 200B in color.

*Leaf apex*.—Abruptly acute.

*Leaf quantity*.—Average of 12 per lateral branch.

*Leaf fragrance*.—None.

*Leaf venation*.—Pinnate, color; upper surface 144B, lower surface a blend of 143A and 146A.

*Leaf margins*.—Finely serrate, very slightly undulate.

*Leaf arrangement*.—Alternate.

*Leaf aspect*.—Flat to very slightly concave and slightly carinate.

*Leaf attachment*.—Petiolate.

*Leaf surface*.—Both surfaces are leathery, smooth, glabrous, and non-rugose, upper surface is glossy, lower surface is matte.

*Leaf size*.—Average of 13.7 cm in length, 5.8 cm in width.

*Leaf color*.—Newly expanded leaves upper surface; 153A, strongly tinged N199C and N199D, newly expanded leaves lower surface; a blend of 153A and 199A, mature upper surface; NN137A and 147A, mature lower surface 146B.

*Petioles*.—Average of 1.2 cm in length and 3 mm in width, smooth and glabrous surfaces, matte, strong, color upper and lower surface 144B.

*Inflorescence description*.—No flowers or fruit produced to date.

It is claimed:

1. A new and distinct cultivar of *Prunus* plant named 'Frerichs 01' as herein illustrated and described.

* * * * *